United States Patent [19]
Scardera et al.

[11] Patent Number: 5,059,625
[45] Date of Patent: Oct. 22, 1991

[54] POLYGLYCIDOL AMINE OXIDE SURFACTANTS HAVING ANTIMICROBIAL ACTIVITY

[75] Inventors: Michael Scardera, Hamden; Frank R. Grosser, Bethany, both of Conn.

[73] Assignee: Olin Corporation, Cheshire, Conn.

[21] Appl. No.: 591,997

[22] Filed: Oct. 1, 1990

[51] Int. Cl.$^5$ .................. A61K 31/13; C07C 283/04
[52] U.S. Cl. .................. 514/644; 252/106; 252/547; 564/297
[58] Field of Search .................. 514/644; 564/297

[56] References Cited

U.S. PATENT DOCUMENTS

| | | | |
|---|---|---|---|
| 2,089,569 | 9/1937 | Orthner et al. | 260/410.6 |
| 2,131,142 | 10/1938 | Orthner et al. | 260/1 |
| 3,437,598 | 4/1969 | De Volder et al. | 252/156 |
| 3,441,508 | 4/1969 | Drew et al. | 564/297 |
| 3,865,628 | 2/1975 | Callahan et al. | 134/2 |
| 4,011,389 | 3/1977 | Langdon et al. | 536/4 |
| 4,048,121 | 10/1977 | Chang et al. | 252/527 |
| 4,062,976 | 12/1977 | Michaels | 514/644 |
| 4,272,395 | 6/1981 | Wright et al. | 252/106 |
| 4,414,128 | 11/1983 | Gofflnet et al. | 252/111 |
| 4,820,820 | 4/1989 | Sebag et al. | 564/297 |
| 4,944,199 | 7/1990 | Scardera et al. | 564/285 |
| 5,023,008 | 6/1991 | Scardera et al. | 252/106 |

FOREIGN PATENT DOCUMENTS

| | | |
|---|---|---|
| 2113732 | 9/1972 | Fed. Rep. of Germany . |
| 2364439 | 7/1975 | Fed. Rep. of Germany ...... 564/297 |
| 2709690 | 5/1978 | Fed. Rep. of Germany . |
| 1308190 | 2/1973 | United Kingdom . |

OTHER PUBLICATIONS

Preliminary data–Poly–Tergent CS-1 Surfactant.
DE2364439-A Derwent.
German Offenlegungsschrift 26 44 289 (Apr. 6, 1978).

Primary Examiner—Glennon H. Hollrah
Assistant Examiner—Susan Treanor
Attorney, Agent, or Firm—Dale Lynn Carlson

[57] ABSTRACT

The present invention relates to novel compounds represented by the formula:

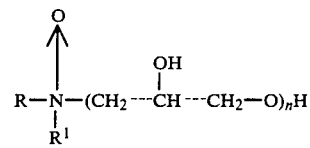

wherein R is an alkyl group having from about 8 to about 18 carbon atoms, and mixtures thereof, n has a value of from 1 to 6, $R_1$ is selected from the group consisting of an alkyl group having from 1 to about 12 carbon atoms, or

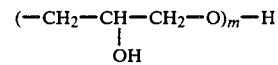

where the sum of n+m=2 to 12. These compounds possess antimicrobial activity and are useful as cleaning agents and preservatives, particularly in water-based functional fluids and surface coating compositions.

8 Claims, No Drawings

POLYGLYCIDOL AMINE OXIDE SURFACTANTS HAVING ANTIMICROBIAL ACTIVITY

FIELD OF THE INVENTION

The invention relates generally to novel compounds having antimicrobial activity, and more particularly to polyglycidol amine oxide surfactants and their use in cleaning compositions.

BACKGROUND OF THE INVENTION

General purpose or all-purpose household cleaning compositions for hard surfaces such as metal, glass, ceramic, plastic and linoleum surfaces are sold commercially in both powdered and liquid form. The powdered compositions consist mainly of builders and buffering salts such as phosphates, carbonates, silicates and the like and these compositions are diluted with water prior to use. While use concentrations of such compositions usually provide good inorganic soil removal, they tend to be deficient in removal of organic soils such as the greasy/fatty/oily soils typically found in the domestic environment. Further, such compositions tend not to be compatible with germicidal ingredients because of the presence of anionic detergents and high concentrations of builder salts.

On the other hand, all-purpose liquid cleaners have met with greater commercial acceptance because they have the advantage that they can be applied to hard surfaces in neat or concentrated form so that a relatively high level of surfactant material is delivered directly to the soils. Because of these advantages, much research and development effort has been expended on formulating all-purpose liquid cleaning compositions which are stable upon storage, have good physical properties and are effective in removing inorganic and organic soils.

Liquid hard surface cleaners generally have been classified into two types. The first type is a particulate aqueous suspension having water-soluble abrasive particles suspended therein, which particles are palpable. Some of the cleaners of this type suffer a stability problem and other cleaners of this type have received poor acceptance by consumers because of their "gritty" feel which causes many people to be reluctant to use then for fear of scratching the surface to be cleaned. The second type is the liquid detergent without suspended abrasive and, seemingly, this latter type is preferred by consumers. While this second type generally is a mixture of surfactant and builder salt in an aqueous medium, the product formulations in the market place have varied widely in composition.

One liquid product which achieved some success was based upon a mixture of soap, alkylbenzene sulfonate and fatty acid alkanolamide plus inorganic builder salts. This liquid product exhibited good temperature stability and a desirable viscosity, but tended to exhibit cleaning disadvantages when compared with another product based upon a mixture of alkylbenzene sulfonate and ethoxylated alkanol plus builder salts. However, the latter composition usually required a high concentration of a lower alkylbenzene sulfonate hydrotrope in order to achieve homogeneity in the presence of builder salt and the inclusion of hydrotrope resulted in lower viscosity and the need of thickening agents.

Other all-purpose liquid products have been prepared which incorporate a solvent such as a terpene. For example, German patent application No. 2,113,732 discloses the use of terpenes as antimicrobial agents in washing compositions. British patent no. 1,308,190 teaches the use of dipentenes in a thixotropic liquid detergent suspension based composition. German patent application No. 2,709,690 teaches the use of pine oil, a mixture of largely terpene alcohols, in liquid hard surface cleaning compositions. U.S. Pat. No. 4,414,128 teaches the use of terpenes with solvents of limited water solubility such as benzyl alcohol in all-purpose cleaning compositions. The terpenes are used to provide cleaning as well as to control sudsing. A similar composition is disclosed in European patent application No. 0080749 which comprises surfactant terpenes, butyl carbitol and builder salts. Again, the terpenes are included for cleaning and as suds regulators.

U.S. Pat. No. 4,272,395 describes a high foaming detergent composition suitable for use in dishwashing and in the cleaning and disinfecting of hard surfaces obtained by combing a quaternary ammonium compound having a formula:

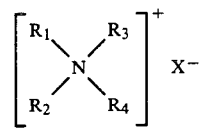

wherein $R_1$ and $R_2$ are alkyl groups each having 9 to 11 carbon atoms, $R_3$ and $R_4$ can each be an alkyl group, an alkylether group or a hydroxyalkyl group having 1-3 carbon atoms, or a benzyl group; and $X^-$ is either $Cl^-$, $Br^-$, $I^-$, $NO_3^-$, $\frac{1}{2} SO_4^{2-}$, $CH_3SO_4^-$, $C_2H_5 SO_4^-$, $\frac{1}{2} HPO_4^{2-}$, or $CH_3COO^-$, and a cosurfactant selected from the group consisting of short chain anionic surfactants having 3-8 carbon atoms in the hydrophobic groups, low alkoxylated nonionic surfactants having 0-4 ethylene oxide and/or propylene oxide groups in the molecule, and mixtures thereof.

Despite the extensive efforts in formulating all-purpose liquid cleaning compositions, there is still a need for a liquid product with both effective cleaning properties and disinfecting properties when applied neat, as well as at various concentrations when used in water. Also such products should be effective at varying water hardness levels, should have desirable foaming characteristics, and should cause little or no spots or streaks in the presence or absence of rinsing. Further, the resultant product should be homogeneous at temperatures from about 5° C. to about 49° C. and should exhibit a desirable viscosity. In addition, such a product cannot be achieved by simply adding a germicidal quaternary ammonium compound to one of the liquid products discussed above because the quaternary compounds are rendered ineffective by the proportions of anionic detergent and/or builder salts present in those compositions.

SUMMARY OF THE INVENTION

In one aspect, the present invention relates to a novel compound represented by the formula:

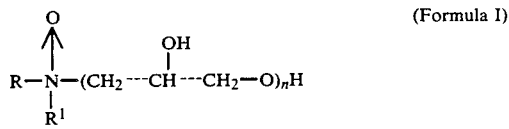

(Formula I)

wherein R is an alkyl group having from about 8 to about 18 carbon atoms, and mixtures thereof, n has a value of from 1 to 6, $R_1$ is selected from the group consisting of an alkyl group having from 1 to about 12 carbon atoms, or

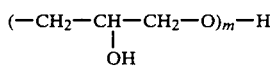

where the sum of $n+m=2$ to 12.

The compounds of the present invention are useful as antimicrobial additives in cleaning compositions.

This and other aspects of the present invention will become apparent upon reading the following detailed description of the invention.

DETAILED DESCRIPTION OF THE INVENTION

The cleaners made using the novel compounds of the present invention can be formulated to exhibit desirable characteristics with regard to both physical properties and performance in use. As to physical properties, the composition may be formulated to be homogeneous, pourable, and free-flowing from the container as manufactured as well as after aging at various temperature. For example, they may be formulated to exhibit a high degree of stability upon storage at normal room temperature of about 24° C. over a period of many months without any appreciable precipitation or formation of layers. Also, when subjected to elevated temperatures of about 38° C. or cooled to about 5° C., the liquid will remain in homogeneous form. As a result of this homogeneity, even when only very small quantities are dispensed, the components will be present in the correct proportions. Furthermore, the liquid may be packaged in any suitable container such as metal, plastic, or glass bottles, bags, cans or drums.

The liquid compositions of the present invention can suitably contain, as the cleaning agent, a wide selection of surfactant(s) which can be anionic, nonionic or cationic, as well as mixtures or blends of nonionic surfactants with either anionic surfactants or with cationic surfactants.

Suitable anionic surfactants which may be employed in the cleaning compositions of the invention include alkylbenzene sulfonates or sulfates, alkyl esters of sulfuric acid or sulfonic acids, alkyl ethoxysulfates, phosphate esters, sulfosuccinates as well as sulfate esters of alkylphenol polyglycidol ethers.

Nonionic surfactants which may be used as cleaning agents include, for example, alkyl phenols, oxyalkylated alcohols, oxyalkylated fatty acids, and oxyalkylated amines where the oxyalkyl groups are, for example, oxyethyl or oxypropyl, alkylphenol polyglycidol ethers, and alkyl polysaccharides among others.

Cationic surfactants which may be used as the cleaning agents include for example, quaternary amine surfactants, alkanolamides, and amine oxides.

Of the three broad types of surfactants employed as cleaning agents only cationic surfactants are known to have antimicrobial properties and these appear to be limited to a selected molecular weight range.

Surprisingly, it has been found that antimicrobial properties in the composition of the present invention are provided by aliphatic amine oxide-polyglycidol adducts represented by Formula I hereinbelow.

The polyglycidol amine oxide adducts represented by Formula I are comprised of a primary or secondary alkyl amine group and the selected number of glycidol groups. Suitable alkyl amines include homogeneous amine groups as well as mixtures such as those sold commercially as coco amines, soya amines, and tallow amines or mixed fatty amines. While the alkyl groups may be branched or linear, where improved biodegradability is desired, linear alkyl groups with minimal branching are preferred.

Polyglycidol amine oxide adducts represented include those of Formula I in which R represents, for example, octyl, nonyl, decyl, hendecyl, dodecyl or coco or lauryl, tetradecyl, pentadecyl, hexadecyl, heptadecyl, octadecyl or stearyl (tallow or soya), and mixtures thereof.

Antimicrobial effective amounts of the polyglycidol amine oxide compounds include those which inactivate or prevent the growth of organisms such as bacteria or fungi. In general cleaning formulations, the polyglycidol amine oxide compound is present in molar ratios to the surfactant present as the cleaning agent of from about 10:1 to about 1:10, preferably at molar ratios of from about 7:1 to about 1:9, with molar ratios of from about 5:1 to about 1:5 being more preferred. The selection of molar ratios of the antimicrobial amine glycidol compound to surfactant is related to the application, institutional use, for example, in hospitals or commercial laundries, may employ compositions having higher molar ratios of the antimicrobial compound.

The cleansing composition of the present invention may also include ingredients such as perfumes, colorants, and sequestering or chelating agents such as ethylenediamine polyacetic acids and their salts incorporated to improve the cleansing properties of the products in hard water.

The preferred form of the cleansing compositions of the present invention is a liquid in which the solvent is water, a water soluble, or a water miscible compound such as an alcohol, glycol or glycol ether. The antimicrobial composition may also be produced in many different forms such as dried granules, flakes, etc., which are well known in the cleansing products industry.

The novel antimicrobial polyglycidol amine oxide adducts of the present invention may be used as a preservative in water-based functional fluids as well as in surface coating compositions in which water is a major ingredient. In these and other applications, the amine glycidol compounds are useful in controlling the growth of bacteria and fungi as well as providing surfactant properties without adversely affecting the color, pH or other physical properties of the surface-coating composition. Suitable amounts of the amine polyglycidol adducts used as a preservative include, for example, those in the range from about 0.000001 to about 5% by weight.

EXAMPLES

The following examples serve to give specific illustrations of the practice of this invention, but they are not intended in any way to limit the scope of this invention.

Example 1

Preparation of a Polyglycidol Amine Oxide Compound

A 500 ml, 3-necked round bottom flask was fitted with a mechanical stirrer, thermometer, nitrogen inlet, dropping funnel and vent. Under the nitrogen atmosphere, Armeen CD[(1)], 15 g (0.075 mole) was placed in the flask and the contents heated to 138° C. Glycidol in an amount of 16.67 g (0.225 mole) was placed in the dropping funnel and glycidol addition to the Armeen CD was initiated at a rate of approximately 0.15 g/minute. Reaction temperature was maintained at 140°–152° C. and glycidol addition was completed in about 2 hours. The reaction mixture was stirred and heated at reaction temperature an additional 2 hours. The flask and its contents were then cooled and the product removed. The product, a 3-mole glycidol adduct of $C_8$–$C_{18}$ aliphatic amines weighed 31.6 g and a 1% solution of this product was soluble and clear in 50% sodium hydroxide solution. This product was referred to as cocamine 3-mole glycidol adduct and its molecular weight was 422.

A 100 ml 3-necked round bottom flask was fitted with a thermometer and water condensed, and a magnetic stirring bar placed in the flask. Cocamine 3-mole glycidol adduct in 50% water, 18.9 g (0.22 m) was placed in the flask. With stirring, the contents were heated to 55° C. at which time 30% hydrogen peroxide, 2.5 g (0.022 m) was added. The reaction mixture was heated for 5 hours; then cooled to ambient temperature. The product, Armeen CD-3m glycidol amine weighed 20.8 g.

[(1)] ARMEEN CD which is a product of Armak Chemicals is a ($C_8$–$C_{18}$ aliphatic amine blend)

Example 2

Another Preparation of a Polyglycidol Amine Oxide

The procedure of Example 1 was repeated in a similar manner. Conditions were as follows:

| Preparation of Armeen CD-4 mole glycidol adduct: | |
|---|---|
| Armeen CD | 280 g (1.4 moles) |
| Glycidol | 414.9 g (5.6 moles) |
| Reaction temperature | 149–153° C. |
| Reaction time | 3 hours |
| Product Weight | 694 g |
| Preparation of the amine oxide derivative: | |
| Armeen CD-4 mole glycidol adduct | 74.5 g (0.15 m) |
| Hydrogen peroxide (30%) | 17.0 g (0.15 m) |
| Reaction temperature | 64–76° C. |
| Reaction time | 2.5 hours |
| Product diluted to 50% active with distilled water weight 160 g. | |

Example 3

Another Preparation of a Polyglycidol Amine Oxide

The procedure of Example 1 was repeated with the following changes in conditions:

| Preparation of Armeen CD-6 mole glycidol adduct: | |
|---|---|
| Armeen CD | 200 g (1 mole) |
| Glycidol | 444 g (6 mole) |
| Reaction temperature | 144–155° C. |
| Reaction time | 4 hours |
| Product Weight | 644 g |
| Preparation of the amine oxide derivative | |
| Armeen CD- 6 mole glycidol adduct | 77.3 g (0.12m) |
| Hydrogen peroxide (30%) | 13.6 g (0.12m) |
| Reaction temperature | 53–66° C |
| Reaction time | 1.5 hours |
| Product diluted to 50% active with distilled water - weight 182 g | |

Properties

The surface tensions (ASTM Designation D1331-56) of the products at 0.1 wt. % concentration were as follows:

| Product of Example 1 | 32.3 | dynes/cm |
| Product of Example 2 | 33.5 | " |
| Product of Example 3 | 35.1 | " |

The surface tension of distilled water is approximately 72 dynes/cm.

All three products were soluble in 50% sodium hydroxide solution.

Antimicrobial Evaluation

Minimum Inhibitory Concentration (MIC's) were determined and compared to a nonylphenol-glycidol based surfactant. The results are shown in attached Table I. MIC tests indicate that these adducts possess significant antimicrobial and antifungal activity.

TABLE I

| | Minimum Inhibitory Concentration (PPM) | | |
|---|---|---|---|
| COMPOUND OF | ESCHERIDIDA COLI (Gram Negative) | STAPHYLOCOCCUS AUREUS (Gram positive) | ASPERGILLUS NIGER (Fungus) |
| Example I | 256 | 32 | 128 |
| Example II | 1024 | 512 | 128 |
| Example III | 2048 | 2048 | 512 |
| Nonylphenol -glycidol | >25,000 | >25,000 | >25,000 |

While the invention has been described above with the references to specific embodiments thereof, it is apparent that many changes, modifications and variations in the materials, arrangement of parts and steps can be made without departing from the inventive concept disclosed herein. Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety in pertinent part.

Having thus described the invention, what is claimed is:

What is claimed is:

1. An antimicrobial composition for use in controlling bacteria and fungi in an aqueous medium consisting essentially of a suitable carrier and an antimicrobial effective amount of a compound represented by the formula:

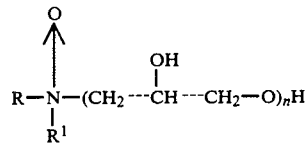

wherein R is an alkyl group having from about 8 to about 18 carbon atoms, n has a value of from 1 to 6, $R_1$ is selected from the group consisting of an alkyl group having from 1 to about 12 carbon atoms, or

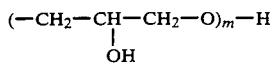

with the proviso that when $R_1$ is

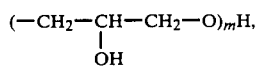

the sum of $n+m=3$ to 12.

2. The antimicrobial composition of claim 1 in which the aqueous medium is a water-based functional fluid.

3. The antimicrobial composition of claim 1 in which the aqueous medium is a surface-coating composition.

4. The antimicrobial composition of claim 1 in which $R'$ represents an alkyl group having from 1 to about 4 carbon atoms.

5. The antimicrobial composition of claim 1 in which R represents decyl.

6. The antimicrobial composition of claim 1 in which R represents dodecyl.

7. The antimicrobial composition of claim 1 in which R represents tetradecyl.

8. The antimicrobial composition of claim 1 in which R represents coco.

* * * * *